US007949386B2

(12) United States Patent
Buly et al.

(10) Patent No.: US 7,949,386 B2
(45) Date of Patent: May 24, 2011

(54) COMPUTER-AIDED OSTEOPLASTY SURGERY SYSTEM

(75) Inventors: Robert L. Buly, Larchmont, NY (US); Bryan T. Kelly, New York, NY (US); Andrew Pearle, New York, NY (US); Carinne Granchi, New York, NY (US); Stephane Lavallee, Saint Martin d'Uriage (FR); Christopher Plaskos, New York, NY (US); Sylvain Besson, Echirolles (FR)

(73) Assignee: A² Surgical, Sailles (FR)

( * ) Notice: Subject to any disclaimer, the term of this patent is extended or adjusted under 35 U.S.C. 154(b) by 934 days.

(21) Appl. No.: 11/688,628

(22) Filed: Mar. 20, 2007

(65) Prior Publication Data
US 2007/0249967 A1    Oct. 25, 2007

Related U.S. Application Data

(60) Provisional application No. 60/784,639, filed on Mar. 21, 2006.

(51) Int. Cl.
*A61B 5/05* (2006.01)

(52) U.S. Cl. ........ 600/427; 600/407; 600/424; 600/426; 600/429; 600/587; 606/53; 606/128; 606/130; 703/11; 345/629; 345/630

(58) Field of Classification Search .................. 600/424, 600/426, 427, 429, 407, 587; 606/128, 130, 606/53; 703/11; 345/629, 630
See application file for complete search history.

(56) References Cited

U.S. PATENT DOCUMENTS

| 5,564,437 | A | 10/1996 | Bainville et al. |
| 6,161,080 | A * | 12/2000 | Aouni-Ateshian et al. ..... 703/11 |
| 6,205,411 | B1 * | 3/2001 | DiGioia et al. ................. 703/11 |
| 6,697,664 | B2 | 2/2004 | Kienzle, III et al. |
| 2003/0176783 | A1 | 9/2003 | Hu |
| 2005/0101966 | A1 | 5/2005 | Lavallee |
| 2006/0161052 | A1 | 7/2006 | Colombet |

FOREIGN PATENT DOCUMENTS

FR    1222636    6/1960

OTHER PUBLICATIONS

Marcos Agus, Andrewa Giachetti, Enrico Gobbetti, Gianluigi Zanetti, Antonio Zorcolo, Bruno Picasso, Stefano Sellari Franceschini, "A haptic model of a bone-cutting burr", 2003, Stud Health Technol Inform, 94: 4-10.*
Rajeev Kelkar, "Normal and abnormal mechanics of the shoulder: Studies of articular geometry, contact and kinematics", 1996, Columbia University Ph.D Dissertation, abstract summary.*

* cited by examiner

*Primary Examiner* — Tse Chen
*Assistant Examiner* — Jason Ip
(74) *Attorney, Agent, or Firm* — Baker Donelson Bearman, Caldwell & Berkowitz, PC (57) ABSTRACT

A method for performing computer-assisted orthopaedic surgery includes the steps of: (1) producing and displaying three-dimensional geometrical models of first and second bones, the first and second bones forming a joint; (2) identifying a zone of impingement between the first bone and the second bone on at least one of the bones; and (3) generating and displaying a color map of at least one surface of at least one bone, the at least one surface being within the zone of impingement, the color map including different colors representing different depths of bone to be removed in order to achieve an increased range of motion between the first and second bones.

23 Claims, 6 Drawing Sheets

COMPUTER-AIDED OSTEOPLASTY SURGERY SYSTEM

CROSS-REFERENCE TO RELATED APPLICATION

The present application claims the benefit of U.S. patent application Ser. No. 60/784,639, filed Mar. 21, 2006, which is hereby incorporated by reference in its entirety.

TECHNICAL FIELD

This invention relates to the field of computer assisted orthopaedic surgery, and more particularly, to osteoplasty surgeries, such as Femoral Acetabular Impingement surgery.

BACKGROUND

Osteoarthritis (OA) is thought to be caused by a combination of intrinsic vulnerabilities of the joint, such as anatomic shape and alignment, and environmental factors, such as body weight, injury, and overuse. In the hip, for example, it has been postulated that much of osteoarthritis is due to developmental anatomic deformities. Recent studies have demonstrated that more subtle anatomic abnormalities, such as acetabular retroversion, acetabular over-coverage, and decreased head-neck offset of the femoral head-neck junction are also important anatomic variants of the hip joint that may lead to pain and OA.

Femoral Acetabular Impingement (FAI) is often classified into two distinct entities, namely, cam impingement and pincer impingement. Cam impingement results from pathologic contact between an abnormally shaped femoral head and neck with a morphologically normal acetabulum. This pattern of impingement is characterized by a femoral head-neck junction which is not spherical anteriorly and has increased radius of curvature. As the hip flexes, this abnormal region engages the anterior acetabulum. The resultant shear forces which result from this contact produces the characteristic anterosuperior chondral injury and associated labral tear. The second type of FAI, pincer impingement, is the result of contact between an abnormal acetabular rim and a typically normal femoral head-neck junction. This pathologic contact is the result of abnormal anterior acetabular "over coverage." This results in decreased joint clearance and repetitive contact between the femoral neck and acetabulum. Ultimately, this repetitive contact causes degeneration of the anterosuperior labrum much like in cam impingement. The injured labrum subsequently may become calcified, further worsening the anterior "over coverage." Additionally, because the anatomic constraint in the native hip is so great, the contact can cause leverage of the head out of the acetabulum posteriorly contributing to a "contre-coup" injury to the posteroinferior acetabulum.

Cam and pincer impingement differ in mechanism, epidemiology, pathoanatomy and surgical management. However, it is not uncommon to see both of these lesions coexisting in a patient with FAI.

The goal of surgical intervention is to relieve the impingement by increasing hip clearance in flexion or some other motions as well as addressing the associated labral and chondral pathology. Surgery is tailored to the underlying anatomic abnormality. Cam type impingement, with prominence of the femoral head-neck region, is addressed on the femoral side with femoral neck osteoplasty or osteochondroplasty. The goal of femoral neck osteoplasty is to recreate the anatomic sphericity of the femoral head and to reduce the prominence of the femoral neck which abuts the anterior labrum and acetabulum. Conversely, pincer impingement lesions often require resection osteoplasty of the acetabular rim with repair of the labrum to its proper anatomic position. When these lesions coexist, osteoplasty of both the femoral head-neck junction and the acetabular rim is required.

Classically, the surgical approach to these lesions has been a formal open surgical dislocation including trochanteric osteotomy. This approach has been espoused for its ability to give an unobstructed 360° view of the femoral head and acetabulum.

Minimally invasive surgery (MIS) and arthroscopic techniques for osteoplasty cause much less morbidity and pain for the patient, and help to promote a much quicker recovery. However, they are significantly more difficult and even impossible for some surgeons to perform, mainly due to the reduced visualization and access in comparison to open techniques. Identifying the impingement zones is problematic due to, for example, the flexion of the hip joint and the interference of surrounding soft tissues. Moreover, it is extremely difficult to visualize the correct amount of bone that should be removed, and to easily verify this without removing too much bone.

In MIS, fluoroscopy is often needed and used to enhance visualization. However, introducing a fluoroscopic arm into the operating room places a great burden on the surgeon, operating room staff, and patient due to the logistic, ergonomic, and radiation issues.

Some have advocated simulating the patients' range of motion on pre-operative images such as computed-tomography (CT) scans or MRI, in order to the physician in planning surgery. However, this approach has several disadvantages. Pre-operative scans such as CT scans require costly imaging equipment and technicians, and they are time consuming for the surgeon. These simulation tools require the transfer and processing of images, using segmentations algorithms which are often not robust and difficult to use. In addition, the simulations cannot take into account the actual kinematics of the patient, and the effects of soft tissues on the patient's real range of motion. The surgeon is also burdened with having to register this preoperative plan to the patient in surgery.

Therefore, an intraoperative tool to help surgeons plan and perform oseteoplasty surgeries, such as, FAI in a more precise and less invasive manner would be an invaluable tool for surgeons and for patients.

SUMMARY

According to one embodiment, a method for performing computer-assisted orthopaedic surgery includes the steps of: (1) using a device to acquire first coordinate points on a surface of a first bone; (2) using the device to acquire second coordinate points on a surface of a second bone that forms a joint with the first bone; (3) producing and displaying a three-dimensional geometrical surface model of the first bone based at least initially on the acquired first coordinate points; (4) producing and displaying a three-dimensional geometrical surface model of the second bone based at least initially on the acquired second coordinate points; (5) moving the first and second bones relative to one another and detecting maximum amplitudes of rotation between the first and second bones; (6) identifying a zone of impingement between the first and second bone on at least one of the bones; (7) displaying as a color map at least one surface of at least one bone model, the at least one surface being within the zone of impingement, the color map including different colors representing different depths of bone to be removed in order to achieve an increased range of motion between the two bones; (8) using a tracked tool to remove bone in the zone of impingement based on real time information provided on the color map; and (9) moving again the first and second bones relative to one another and detecting an increased amount of rotation between the first and second bones.

In another aspect, a method for performing computer-assisted orthopaedic surgery includes the steps of: (1) producing and displaying three-dimensional geometrical models of first and second bones, the first and second bones forming a joint; (2) identifying a zone of impingement between the first bone and the second bone on at least one of the bones; and (3) generating and displaying a color map of at least one surface of at least one bone, the at least one surface being within the zone of impingement, the color map including different colors representing different depths of bone to be removed in order to achieve an increased range of motion between the first and second bones.

These and other aspects, features and advantages shall be apparent from the accompanying Drawings and description of certain embodiments of the invention.

DETAILED DESCRIPTION OF CERTAIN EMBODIMENTS OF THE INVENTION

The system according to one exemplary embodiment of the present invention is made up of a number of working components that interact with one another to perform a number of different operations. The headings below are merely for highlighting the various components of the present system, as well as the various operations or tasks performed by the system. As such, the headings are not limiting of the scope of the present invention.

Camera and Tracking

Figure 1:
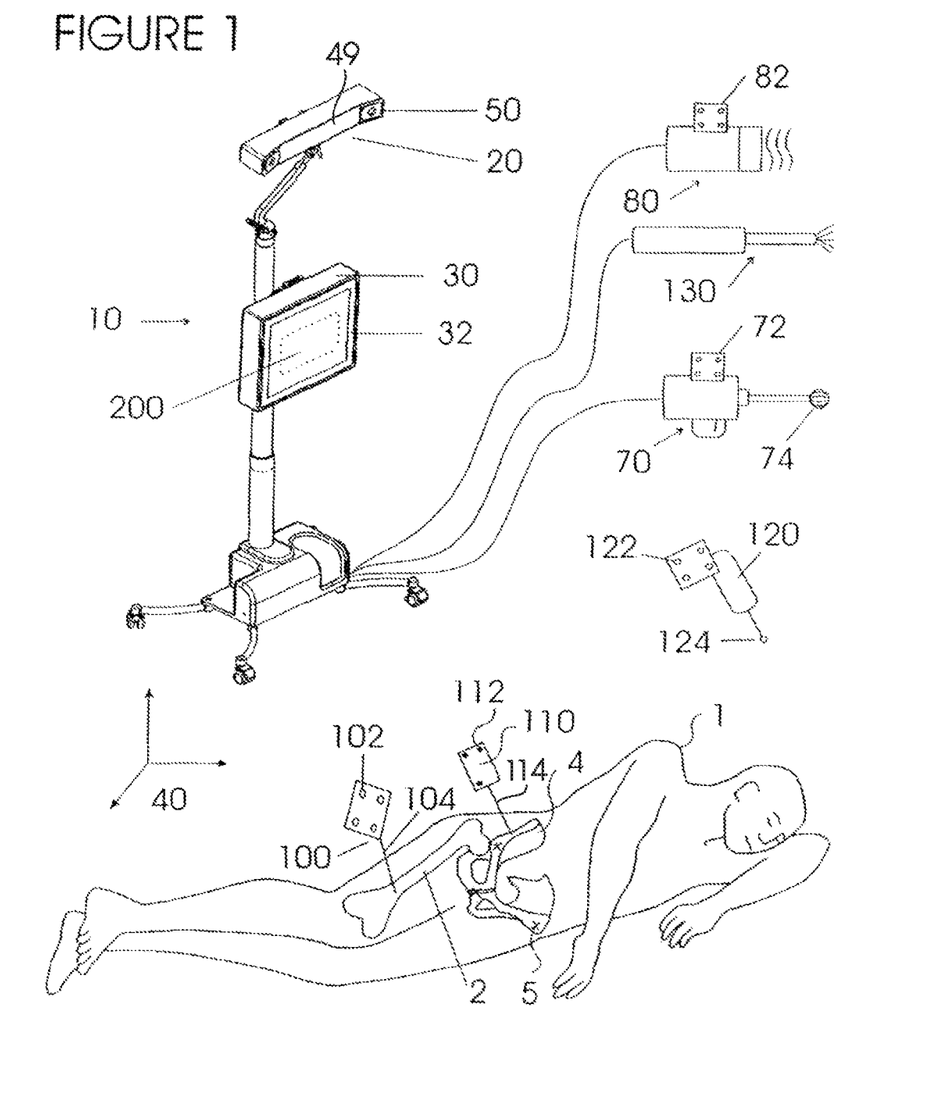
FIG. 1 is a perspective view of a computer-assisted orthopaedic surgery (CAOS) system according to one embodiment of the present invention.

Referring now to FIG. 1, a computer-assisted orthopaedic surgery (CAOS) system 10 is schematically shown. The CAOS system 10 is configured for performing joint preserving surgeries, such as osteoplasties and femoral acetabular impingement surgery. The system includes a suitable position measuring device 20 that can accurately measure the position of marking elements in three dimensional space. The position measuring device 20 can employ any type of position measuring method as may be known in the art, for example, emitter/detector or reflector systems including optic, acoustic or other wave forms, shape-based recognition tracking algorithms, or video-base, mechanical, electromagnetic and radio frequency systems. In an embodiment, schematically shown in FIG. 1, the position measuring system 20 is an optical tracking system that includes at least one camera 49 that is in communication with a computer system 30 and positioned to detect light reflected from a number of special light reflecting markers or spheres shown at 50.

Detecting and determining the position and orientation of an object is referred to herein as "tracking" the object. To provide precision tracking of objects, markers can be rigidly connected together to form reference bodies, (e.g., 100, 110), and these reference bodies can be attached to bones, tools and other objects to be tracked. One such device that has been found to be suitable for performing the tracking function is the Polaris™ system from Northern Digital Inc., Ontario, Canada.

The position measurement device 20 is described in greater detail in a number of publications, including U.S. Pat. No. 5,564,437 and United States patent application publication No. 2005/0101966 A1 by S. Lavallee, both of which are incorporated by reference in their entirety.

The relative position of the patient's bones, such as the patient's femur 2 and the patient's pelvis 4, can be determined and tracked by attaching reference bodies 100, 110, which include respective markers 102, 112. Reference bodies can be attached to bones or tools using pins or screws (104, 114) or various quick release mechanisms. The reference bodies can also be shaped in the form numbers (e.g. "1", "2", "3" . . .) or alphabetical letters, such as "F" for Femur, "I" for Iliac, "P" for pointer, and so on, so as to avoid confusion as to which reference body should be attached to which bone or tool.

The tracked objects and there relative positions can be displayed on a screen that is connected to the computer system 30. In an embodiment, the display is a touch screen which can also be used for data entry.

The position measurement device 20 includes a number of different tools that are used at different locations and perform different functions as the system 10 is operated to yield optimal osteoplasty data and information. These tools include the above described markers 50, which act as landmark markers, as well as other tools, such as a milling or burring device 70 having at least three markers 72, which is an example of an object trackable by position measuring device 20. The system also includes a pointer 120, with markers 122, which can be used to digitize points on the surfaces of the femur 2 and pelvis 4.

The burring device 70 also has a burr tip (drill tip) 74 having a known spatial shape and relationship relative to markers 72. Position measuring device 20 determines the position and orientation of markers 72 in the three dimensional coordinate system 40. Based upon the known spatial relationship between burr tip 74 and markers 72, the position and shape of burr tip 74 is determined.

Computer 30 is preferably configured to allow at least one of intra-operative 3-D shape model reconstruction and medical image data, like fluoroscopic images and ultrasound data, to be used in planning of an area to be burred in a bone. The depth of the bone being removed by the burring device 70 can be monitored and displayed by the computer 30. Thus, the burring depth can be compared to the previously planned burring depth to allow the practitioner to minimize deviations between the actual procedure and the preoperative plan. In one embodiment the burring device 70 is guided to allow the computer 30 to control the burring depth.

As previously mentioned, the plurality of reference bodies 100, 110, are used for determining the position and orientation of an individual's bone in the three dimensional coordinate system 40. The reference bodies 100, 110 are preferably rigid and include respective markers 102, 112, which are preferably configured to emit energy. Each reference body 100, 110 preferably includes a respective attachment element, such as pins or screws 104, 114, with which the reference bodies can be releasably attached to a bone. For example, the reference body 100 is shown as being attached to femur 2. The position and orientation of femur 2 can be determined based upon the position and orientation of markers 102 attached thereto. Markers 102, 112 are sufficient to establish the position and orientation of the rigid bodies 100, 110 within the coordinate system 40.

Landmark Digitization

The system 20 also includes the pointer 120 and endoscope 130, which cooperate to allow a practitioner to digitize landmarks of the femur 2 and pelvis 4. Digitizing a landmark comprises determining the position of the landmark in the three dimensional coordinate system, as discussed below. The pointer 120 includes the markers 122, which allow the position and orientation of the pointer 120 to be determined in the three dimensional coordinate system 40. The pointer 120 preferably includes a pointer tip 124 having a known spatial relationship to the markers 122. Based upon the known spatial relationship, the position of the pointer tip 124 can be determined from the position and orientation of the markers 122.

In an embodiment of the invention, landmark points and or directions are digitized with respect to the femur 2 and pelvis 4 with the pointer and are stored in the computer. Preferably, an anatomical coordinate system for the femur and the pelvis is defined based on at least a portion of the acquired data. The coordinate system could also be defined at least partially using kinematic methods, such as fitting a sphere to a trajectory (e.g. fitting a sphere to the trajectory of the femur as it is moved relative to the pelvis). From these trajectories points or planes can be computed that correspond to the anatomy, such as the kinematic hip center. Possible landmark points for the femur include but are not limited to the femoral medial and lateral epicondyles, the center of the patella, a point acquired on the tibial crest with the leg in flexion, the most lateral point of the greater trochanter, hip center, femoral head bone surface areas, etc. For the pelvis, points such as the homo-lateral or contra-lateral anterior superior iliac spine 5, anterior horn, points on the acetabulum lip, etc., could be used.

System User Interface

Figure 2:
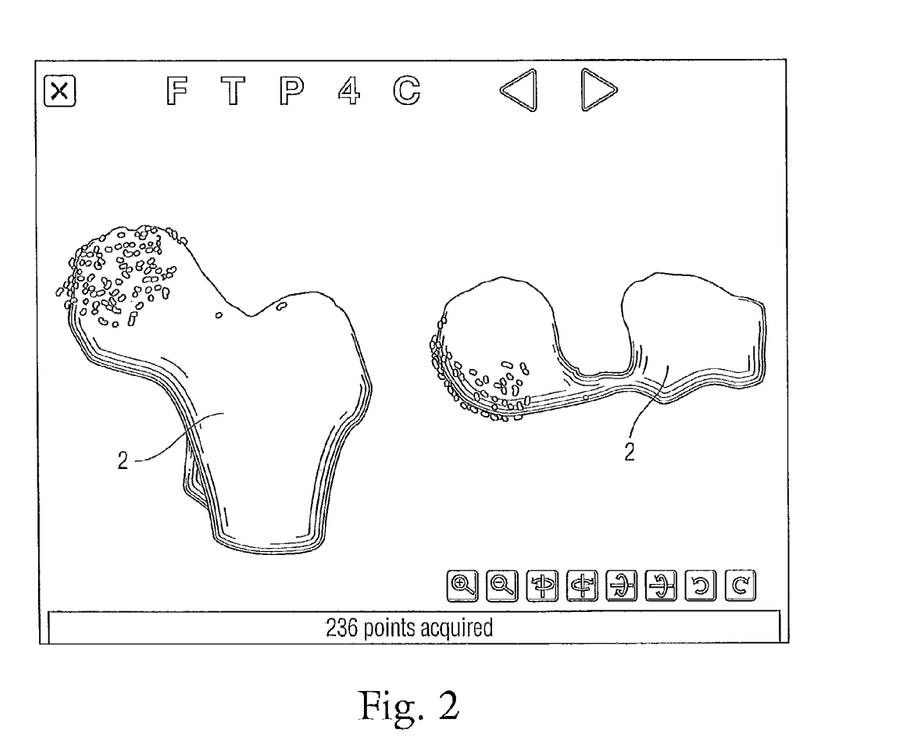
FIG. 2 is a perspective view of an image of a femur bone showing the acquisition of data points along the femur using a pointer or the like of the CAOS system to provide a model of the femur using bone morphing techniques.
Figure 3:
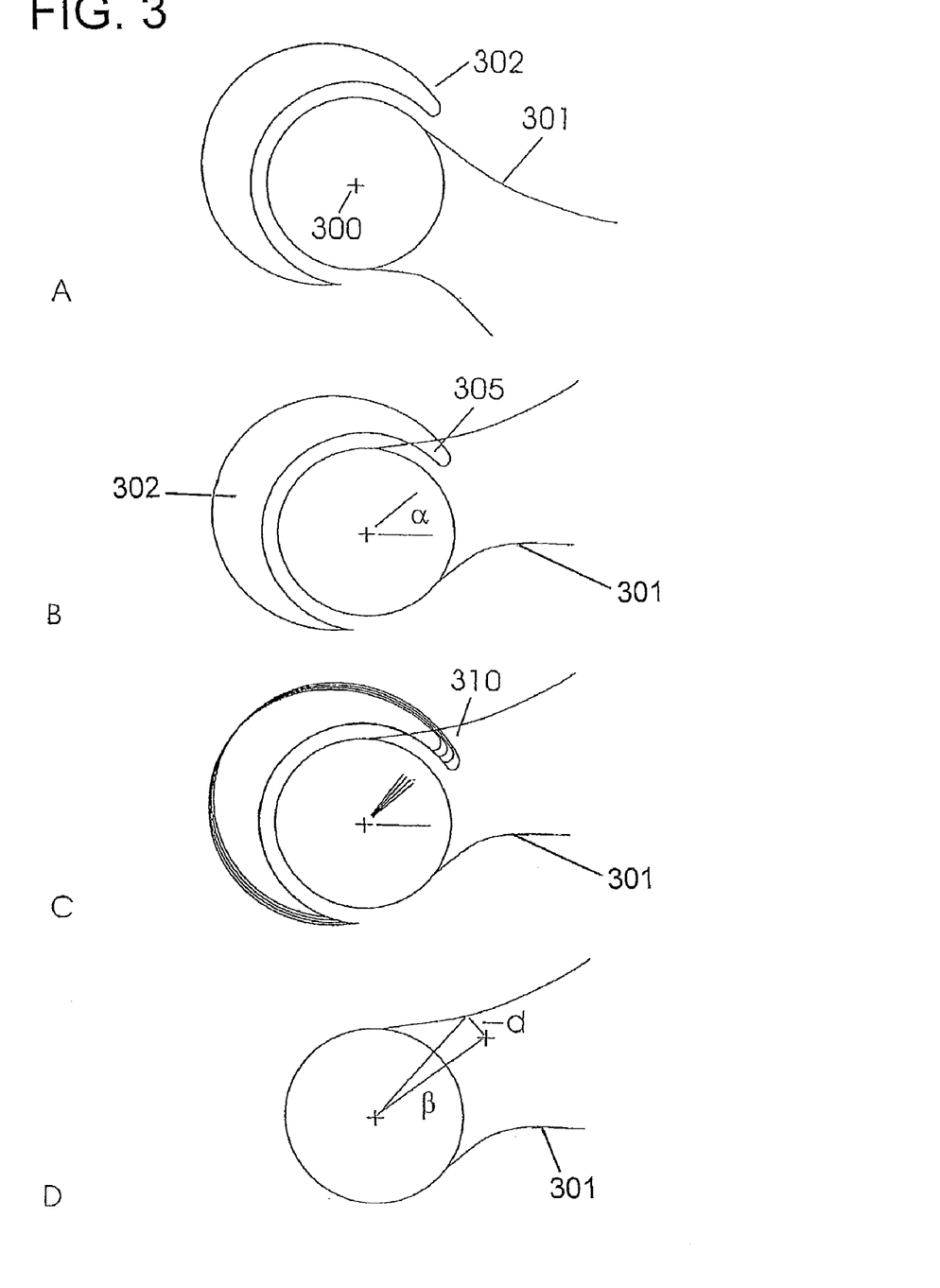
FIG. 3A is a cross-sectional view of an image of a femur bone in a first position relative to the acetabulum surface of the pelvis.
FIG. 3B is a cross-sectional view of the femur bone moved to a second position relative to the acetabulum.
FIG. 3C is a cross-sectional view showing the femur bone is a series of different positions relative to the acetabulum.
FIG. 3D is a cross-sectional view showing the relationship between any bone to point to the hip center.
Figure 4:
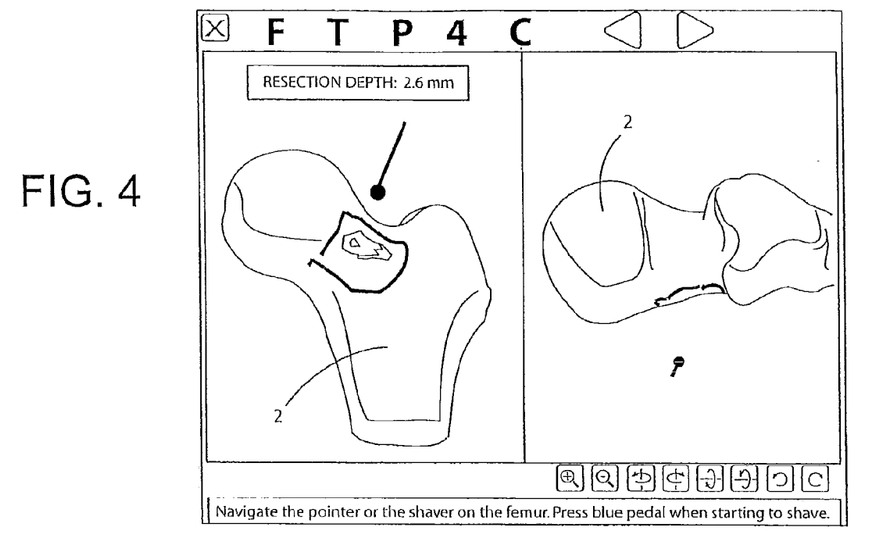
FIG. 4 is a perspective view of an image of a femur with a probe being used to define a potential impingement zone.

Now referring to FIGS. 2-4, the osteoplasty system 10 is preferably an integrated system in which each of the tools is in communication with a master controller, such as the computer 30, which serves to collect all of the data from the individual tools and then process the data to calculate various measurements that are displayable to the physician. The osteoplasty system 10 accordingly includes a user interface 200 (FIG. 1) that is supported by software in the computer 30. The user interface 200 is configured to assist and walk the physician through the osteoplasty procedure to obtain optimal results and to assist the physician in determining what the best course of action is in terms on providing and optimizing the range of the motion of the hip.

A main user interface page or screen is preferably displayed on the display 32 (FIG. 1) of the computer 30. The main user interface screen can include a section where the patient's name or other identifying information can be entered using a keypad or the like. The main screen can also include a hip indicator box or region which the physician or operator can highlight whether the procedure is being performed on either the left hip or the right hip. Furthermore, the main screen includes indicator boxes in which the physician or operator can highlight whether the procedure is being performed on the femur, acetabulum, or both. The main screen includes a region where tool related information can be entered, as by highlighting a "spherical burr" box, etc. The main screen also includes a section where the burr diameter can by entered with keypad. The system can also allow the user to select a burr geometry and size from a database of burring tools stored in the computer memory 30. The main screen further includes a section or region where different operations to be performed during the procedure can be selected by the physician. For example, a region can list a number of different options that can be performed to test the state and kinematics of the hip, especially the range of motion thereof, to assist in diagnosing a hip condition, such as a zone in the hip in which there is a potential impingement of the femur with the acetabulum.

In addition, a screen can be provided to check the visibility of the reference bodies and in particular, one or more viewing areas can be displayed on the screen 32 (such as one area relating to depth of sight and another area relating to a radius of sight). If the object to which the reference body is attached is visible to the system, then an icon, such as a letter or number, will appear and be displayed and be visible in one or more of the viewing areas. It will be appreciated that the object should be visible in all viewing areas to ensure proper working of the system.

Pointer & Burr Calibration

Before the pointer 120 is used to determine any position taken by its tip 124, the positioning measuring device 20 is calibrated. For example, the pointer 120 is calibrated by placing the pointer tip 124 in a cone that is integrated into reference body 110. The position of the cone relative to reference markers 122 is known. Therefore the position of the pointer tip 124 relative to markers 122 is now measured and stored in the computer 30. The pointer 120 fitted with markers 122 interacts with the detection system so as to precisely determine any position taken by its tip 124. Similarly, a spherical burr tip (drill tip) 74 of the burring device 70 can be calibrated by selecting precisely the external diameter of the burr tip 74 and then placing the burr tip in the calibration cone. Alternatively, the axis and the tip of the burr can be calculated using known methods. If the burr tip 74 has a known complex shape which is not spherical at the bone contact, its exact shape is entered into the computer memory and many variations of the calibration process can be developed to take the exact shape of the burr tip 74 into account accordingly.

Attachment of Rigid Bodies

To perform computer assisted osteoplasty surgery, especially femoral acetabular impingement, using the present system 10, the reference body 100 is attached to the femur 2 at a selected point, as by screwing the reference body 100 into the bone with screw 104. The reference body 100 includes the first set of at least 3 reflective markers 102 that are thus fixed to the femur 2 at the point. Similarly, the reference body 110 is attached to the pelvis 4 at a selected point by screwing the body 110 into the bone with one or several screws 114. The reference body 110 includes the second set of at least 3 reflective markers 112 that are likewise fixed to the pelvis 4, if the acetabulum option has been chosen at the beginning of the procedure. Since the reference bodies 100, 110 are fixed to the bones 2, 4, the pointer tip 124 can be used to point at any given point on bone 2, 4, the position of which is precisely taken by its tip 124. Then, it is possible using a conventional data processing system to determine the vector connecting the point where the respective bodies 100, 110 attach to the bones 2, 4 to the point of the tip 124, and therefore, locate any given point for any position of the femur 2 or pelvis 4.

There is a plurality of methods in which an anatomical coordinate system can be setup by the surgeon. According to one exemplary method, a number of different reference points are obtained. For example, the pointer tip 124 is used to digitize the medial and lateral femoral epicondyles and the most lateral point of the greater trochanter by placing the tip 124 at these bone location which is determined and stored by position measurement system 20. The midpoint between the medial and lateral femoral epicondyles can be used for the knee center. Alternatively, a point digitized on the center of the patella with the knee in flexion can be used. The center of the hip can also be found by rotating the femur with respect to the pelvis and measuring the relative motion of the bones as the surgeons manually manipulates the leg. The hip center in the femoral reference frame can also be found without attaching a reference body to the pelvis by known means. One such known method is to search for the point in the femoral reference frame that has a minimal displacement in the reference frame of the camera. A point on the anterior portion of the tibia (such as the tibial crest or ankle center) with the leg flexed can also be acquired in the formal reference frame, and combined with the knee and hip center, used to construct the sagittal plane of the femoral coordinate system. The mechanical axis is defined as the axis joining the hip and knee centers. The frontal plane can be defined as a plane perpendicular to the sagittal plane and coincident with the knee and hip centers. The transverse plane can be defined as the plane perpendicular to the frontal and sagittal planes and coincident with the hip center. These points can be used easily to build an anatomical 3-D coordinate system attached to the femur. Similarly for the pelvis, one can use 2 points on the pelvis iliac crests and 1 point taken on the symphysis to create a 3D anatomical pelvis coordinate system. Many variations are possible.

Figure 6:
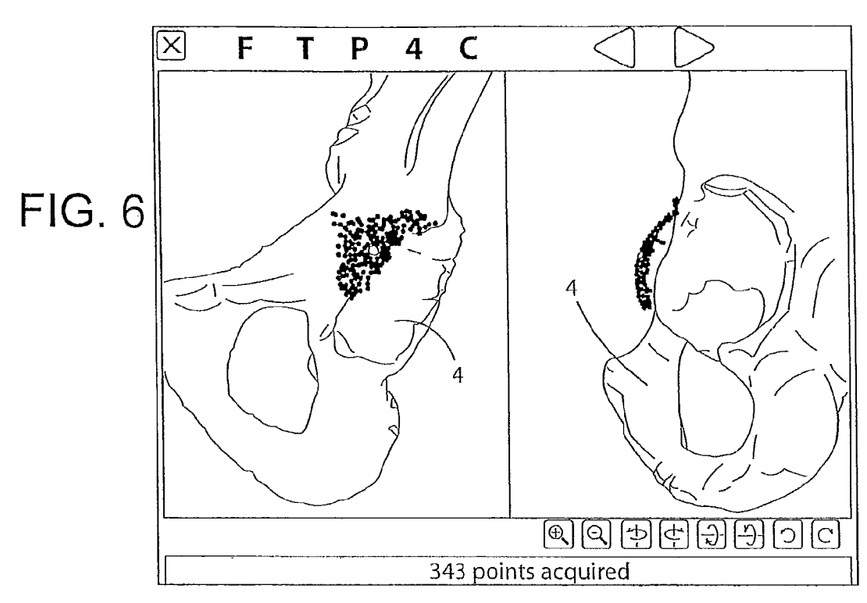
FIG. 6 is a perspective view of the acetabulum surface showing the acquisition of a number of data points thereon using a pointer or the like of the CAOS system to provide a model of the acetabulum using bone morphing techniques.

Acquisition or data points are taken for the femur bone 2 (FIG. 2) and more particularly, the pointer 120 is moved along the surface of the femoral head of the femur bone 2 in order to measure the size of the femoral head, which can be approximated as a sphere. A picture of a sphere is preferably shown on the screen during the acquisition, with the acquired points being super imposed on the sphere in real time as they are acquired. The size of the sphere can also be changing in real time according to points acquired by continuously fitting a sphere to the acquired points. Thus, when the size of the sphere has grown stable and no longer changes, acquisition can stop automatically and the interface can progress directly to the next screen. Next, additional selected surfaces of the pelvis 4 and the femur 2 are investigated and data points are taken and more particularly, the acetabular rim surface of the pelvis 4 is digitized using the pointer 120. FIG. 6 shows a collection and representation of a number of points that have been digitized on the acetabulum lip.

In all of these steps, the digitization occurs by locating and logging a selected bone surface point in the three dimensional coordinate system 40 and by using the data processing system. In other words, the pointer 124 is moved along the bone surface and coordinate data are As previously mentioned, the pointer 120 can be actuated to begin data acquisition by simply activating an actuator, such as a foot pedal in which case it is merely depressed by the physician. The above described digitizing process can be thought of as a landmark acquisition process. Thus, according to an embodiment of the present invention, landmark points and/or directions are digitized with respect to the femur 2 and the pelvis 4 utilizing the pointer 120 and are stored in the computer 30. There are a plurality of methods to set-up anatomical coordinate systems on the bones. Preferably, an anatomical coordinate system for the femur 2 is defined based on at least a portion of the acquired data. For the pelvis an anatomical coordinate system is defined by finding a correspondence between the digitized landmark points and corresponding points on a deformable model of the pelvis, described in more detail below. The model of the pelvis includes the transformation between the digitized landmark points and the anatomical coordinates system. Thus, the anatomical coordinates system of the pelvis 4 is known. The coordinate system can also be defined at least partially using kinematic methods, such as fitting a sphere to a trajectory (e.g. fitting the sphere to the hip motion trajectory). As discussed in some detail above, possible landmark points include, but are not limited to, the femoral epicondyles, the most lateral point on the greater trochanter, the hip center, the homo-lateral or contra-lateral anterior superior iliac spine, anterior horn, points on the acetabulum lip, etc. The data acquisition points can be used to determine other information, such as, locating a mechanical or neck axis of the femur 2. Additionally, when more accuracy is needed, the ultrasound probe 80 can be used to digitize anatomical or landmark points, as described in more detail below.

Echomorphing

In some surgeries, such as arthroscopic surgeries, it is advantages to place the portals in a particular position on the patient 1, relative to the joint being operated on, to maximize visibility of the joint with the endoscope and minimize trauma to patient. Prior to making the incision into the joint, ultrasound data can be acquired with ultrasound probe 80. The ultrasound probe 80 has a reference body 82 attached and can be tracked in space by camera 49 and position measuring device 20. The position of the ultrasound image plane is precalibrated or calibrated directly in the operating room and known with respect to the reference body 82. The relationship between ultrasound image pixel size and location, and real distance in mm is also precalibrated or calibrated directly in the operating room. Thus, the position of the ultrasound image plane, and any pixel the ultrasound image plane, is known in reference coordinate system 40. Such uses of ultrasound or echographic probes are known and can be found in a number of documents, including U.S. Pat. No. 5,447,154, which is hereby incorporated by reference in its entirety. The ultrasound probe 80 is connected to the system computer 30 and thus the ultrasound images can be transferred and processed by the system computer 30 and displayed on the screen 32. Thus, ultrasound images can be recorded relative to bones 2 and 4, and structures, such as, bone surfaces or soft tissues can be identified in the images and thus their positions are known in reference coordinate systems 40 and the bone anatomical coordinate systems. The identification of tissue structures such as bone surfaces can be performed automatically by the navigation computer 30, using known methods as published in the literature, such as active contour segmentation methods or 'SNAKES'. Some examples of such previous methods used to identify bone surfaces in ultrasound images can be found in the following documents:

A Fully Automated Method for the Delineation of Osseous Interface in Ultrasound Images" by Vincent Daanen, Jérôme Tonetti, and Jocelyne Troccaz, in Medical Image Computing and Computer-Assisted Intervention—MICCAI 2004: 7th International Conference Saint-Malo, France, Sep. 26-29, 2004 Proceedings, Part I, Editors: Christian Barillot, David R. Haynor, Pierre Hellier, pages 549-557, LNCS, Springer 2004;

Ultrasound Registration of the Bone Surface for Surgical Navigation" by D. Amin, T. Kanade, A. M. DiGioia III, and B. Jamaraz (Computer Aided Surgery Vol. 8, No. 1, January, 2003, pp. 1-16); and Computer Understanding Bone Responses in B-Mode Ultrasound Images and Automatic Bone Surface Extraction Using a Bayesian Probabilistic Framework" by Ammet K. Jain and Russel H. Taylor, Medical Imaging 2004: Ultrasonic Imaging and Signal Processing published by Walker, William F.; Emelianov, Stanislav Y., Proceedings of the SPIE, Volume 5373, pp. 131-142 (2004). Each of the above cited references is hereby incorporated by reference in its entirety.

Doppler or color doppler analysis of the ultrasound images can also be used to identify the location of vessels. In addition, three dimensional models of the bone surfaces can be reconstructed using the segmented bone surface contours in the ultrasound images and deformable morphing-based methods, as described in more detail below. It is also possible to check automatically that the segmented data on ultrasound images are consistent with an a priori approximate model of the bone and therefore to reject false data accordingly and then to reiterate the process. It is also possible to ask the user to collect more images in anatomical areas where the model needs to be reconstructed in 3 dimensions with some predefined degree of accuracy. Using these images and models, the surgeon can navigate the position of various tools such as the pointer or a scalpel in order to place the portals or to make the incision precisely with respect to the joint or other identified anatomy, such as the femoral head/neck junction.

Bonemorphing

In an embodiment of the present invention, three dimensional geometrical surface models of the bones are provided by image-free means. Preferably, these models are obtained by adjusting a deformable model of the bone to points acquired on the bone surface. Examples of some known methods of carrying out this task can be found in the following references:

Building a complete surface model from sparse data using statistical shape models: application to computer assisted knee surgery" by M. Fleute and S. Lavallée, published in Medical Image Computing And Computer-Assisted Intervention—MICCAI'98, Spinger-Verlag LNCS Series, pages 880-887, October 1998;

Fleute M. Lavallee S, Julliard R. Incorporating a statistically based shape model into a system for computer-assisted anterior cruciate ligament surgery. Medical Image Analysis. 1999 September; 3(3):209-22; and United States patent application publication No. 2005/0101966 A1 by S. Lavallee.

Each of the above listed references is hereby incorporated by reference in its entirety. Other known methods of obtaining geometrical bone models in surgery exist however (for example, matching medical image data such as CT, MRI, etc, to points acquired with a pointer or an ultrasound probe). Another way is to morph a statistical model to information obtained by a few X-ray or fluoroscopic images, such as is described in French Patent Publication No. FR1222636 entitled 'Reconstitution de surfaces en trois dimensions par utilisation de modéles statistiques' by M. Fleute and S. Lavallée, which is hereby incorporated by reference.

In particular, the three dimensional shapes of the involved bones may be provided with image free techniques, such as, using bone morphing software which is capable of extrapolating very few range data to obtain a complete surface representation of an anatomical structure (e.g. a bone). The specific details of bone morphing are set forth in the above references but in general, a complete surface model is built from sparse data using statistical shape models. In particular, the model is built from a population of a number of specimen (points), such as femur or pelvis points, that are digitized and collected (See FIGS. 2 and 6). Models obtained from pathologic specimens may also be used. Data sets are registered together using an elastic registration method (e.g. the Szeliski and Lavallee method) based on octree-splines. Principal component analysis (PCA) is performed on a field of surface deformation vectors. Fitting this statistical model to a few points is performed by non-linear optimization. The different methods and algorithms can be combined and weighted respectively to create an optimal result in a given situation. Similarly the parameters of the algorithms must be tuned and adjusted to different situations. Results can thus be presented for both simulated and real data. This method is very flexible and can be applied to any structures for which the shape is stable.

In an embodiment of the invention, representations (bone morphs) of the femur and pelvis bones, or a portion thereof, are displayed on the screen 32. These models move on the screen 32 in real time based on the motion of tracked femur 2 and pelvis 4. In an embodiment of the invention, the system guides the surgeon in manipulating the hip, by using the bone representations as visual aids. Hip manipulations are preferably preformed to identify joint motion ranges.

In other words, the present system preferably is configured to collect data with the pointer 120 or ultrasound probe 80 in order to perform bone morphing operations or procedures to thus obtain three-dimensional geometrical surface models of the bones. FIG. 2 shows representative bone morphing for the femur 4. Preferably, the representation of the bone on the display 32 of the computer 30 includes shading or some other type of indicator that highlights the areas of the bone that have increased accuracy due to the physician having collected a number of data acquisition points in this region. The areas where more data points were collected are shaded differently or displayed in a different color and the accuracy of the bone morphing (i.e., femoral bone morphing) on the cartilaginous and bony surface can be checked (as by highlighting icons that are displayed). Areas of the bone that have not been scanned using the pointer 120 are simulated using conventional extrapolation techniques as commonly found in bone morphing techniques and systems.

Accordingly, target locations of the femur 2 are digitized and as illustrated in FIG. 2, the neck and head of the femur 2 are preferably digitized as shown in FIG. 2. On the display screen, the system preferably indicates where the pointer 120 has traveled and collected data acquisition points as by providing a visual colored point representation on the screen. Bone morphing for the femur 2 is performed. Shading or some other type of indicator can be used to highlight the areas of the bone that have increased accuracy due to the physician having collected a number of data acquisition points in this region.

Target locations of the pelvis are digitized. On the display screen, the system preferably indicates where the pointer 120 has travelled and collected data acquisition points as by providing a visual colored point representation on the screen. In particular, zones which are suspected to be potential areas of impingement on the acetabular rim are digitized and morphed. Collecting a large amount of points in these areas will assure a high accuracy. Bone morphing for the pelvis is performed. Shading or some other type of indicator can be used to highlight the areas of the bone that have increased accuracy due to the physician having collected a number of data acquisition points in this region.

The collection of bone surface points can be also performed using the burring device 70 directly without using a specific extra pointer.

The accuracy of each of the bone morphing of each of the femur and the acetabulum can be checked using the pointer 120.

Fluoroscopy

Although the system does not strictly require the use of an ionizing imaging means, a tracked C-arm (not shown) or other intra-operative imaging modality could be also connected to the system and fluoroscope images can be acquired and displayed on the navigation screen. In addition, 3D C-arms such as the ISO-C 3D system marketed by Siemens could also be used to display a reconstructed image volume. The connection and use of such imaging devices to CAOS systems is known (see, for example, U.S. Pat. No. 6,697,664 by Kienzle et al., which is hereby incorporated be reference in its entirety). Images of the patient anatomy can be acquired and displayed on the navigation screen 32, and the position of calibrated and navigated tools such as the pointer 120 with tip 124 can be displayed and projected overtop of the acquired images. Anterior-Posterior and lateral views can be taken and used to aid the surgeon in selecting points on the bone or soft tissue anatomy, such as the most lateral point on the greater trochanter of the femur, or the entry point of an arthroscopic portal. Anatomical points can also be entered into the system by selecting them directly on the images using the touch-screen 32.

The computer system can also contain an algorithm that uses the images to assist morphing of the bone model. For example, any algorithm can be employed to extract the bone contours on the images, such as the algorithm commonly known as the 'Canny' edge detector, or any active SNAKE algorithm. The segmented contours can be used as inputs into the BoneMorphing algorithms, to assist the surgeon in acquiring sufficient surface data for Morphing. These contours could supplement or even replace the surface digitization steps with the digitizing probe 120. The Morphing model can be used to aid the segmentation algorithm in an iterative process. For example the morphing model could be used to guaranty the robustness of the segmentation by helping to assess whether or not a segmented image contour really lies on the surface of the bone and is not a false positive. Shape similarity measures or deformation energy measures or intensity gradient measures could be used alone or in combination to relate the process. Alternatively, landmarks such as the femoral head center and surface and most lateral point on the greater trochanter can be identified on the images to determine the initial attitude of the bone model, and then an automatic morphing process can be launched which deforms the model until it matched the silhouette of the bone on the images. As mentioned above intensity gradient information or edge detector techniques can be used to match the model to the images. See French Patent Publication No. FR1222636 and U.S. patent application Ser. No. 10/088,772, which are hereby incorporated by reference in its entirety. The process can also be semi-automatic the surgeon can input information on the touch-screen. For example, he can identify boundary areas where the bone lies, or points on the bone contours, or regions where the morphing is inaccurate and does not match the images (for example, if the algorithm has fallen in a local minima due to a falsely detected contour), in which case the morphing can be refined in those areas. Bone pins 104 or reference markers 102 in the images can also be identified and excluded from the morphing algorithm.

At any time the morphing model can be superimposed over the bone images, allowing the surgeon to gauge the accuracy of the morphing. Multiple views can be shown. As will be described in more detail later on, when the bone surface is altered with a burr, the surgeon can directly visualise how the bone has been altered and much bone has been removed by comparing the remorphed surface to the underlying image of the original unaltered bone. Calibrated probes 120, burrs 70, arthroscopes 130, scalpels and instruments can all be visualised on the screen overtop of the images and relative to the bone model.

Clock Display

Figure 9:
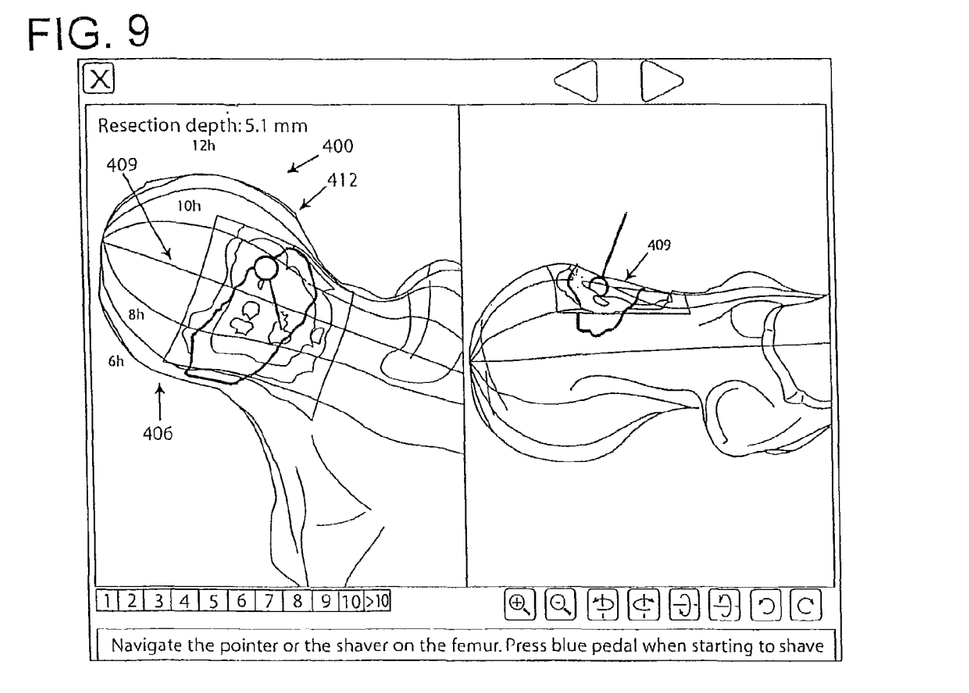
FIG. 9 is a perspective view illustrating real-time milling of the femur with clock reference.

Referring now at FIG. 9, two views of the femoral model are displayed, with a clock reference 400 including contours projected on the 3D bone surface corresponding to 12' (412), 11', 10', 9' (409) ... 6' (406), ... 1' and so on. Contour lines are divided radially from the clock center with equal spacing, as in a real clock. The clock contours are superimposed onto the femoral and acetabular bone surfaces to help the surgeon know where he is on the femoral surface and to know where the position of his tools are relative to the anatomy. The center of the clock reference can be defined on the femur and on the acetabulum by using the center of the hip, as described above. The orientation of the clock reference can be defined on the femoral head and neck by selection of an anatomical point with pointer tip 124 that corresponds to a particular hour on the clock, such as 12 or 9 or 6 o'clock. The anatomical coordinate planes can also be used in combination with a point (for example the frontal plane in combination with the most proximal point in an area of the femoral neck, head, head-neck junction, or greater trochanter). Such points can be selected with the aid of the fluoroscopic or echographic images displayed on the screen.

For example, using the anterior-posterior fluoroscopic view, the surgeon can place his probe on a point on the femoral neck or head corresponding to the 12 o'clock position, and can verify on the images that this point corresponds to the most proximal point in the anterior-posterior X-ray view, or the midpoint of the neck in the lateral view. Similarly, a reference point can also be chosen on the acetabulum, such as the most proximal summit point on the acetabular rim.

The system preferably suggests a clock orientation intelligently and automatically, and allows the surgeon to check and validate or adjust this suggest orientation as he deems necessary. One method of defining the clock reference automatically for the femur is to use the anatomical coordinate system defined by the mechanical axis of the femur (ie the vector joining the center of the femoral head and the center of the knee and determined previously). In particular, the most proximal areas of the femur can be determined by searching for particular points in the model that have the highest coordinate the proximal direction. The mechanical axis can be projected through the femoral head surface to determine one point on the 12' contour. Other information can be used to determine the direction of the contours, such as the most lateral point selected on the femoral trochanter, or the frontal plane direction. Similarly, maximum dimensions in particular directions can be used (such as in the anterior and posterior directions in the area of the neck) and averages of all points can be taken to construct the clock hour references.

Alternate representations of the clock can be envisioned. For example, in a lateral view of the femur or in a view perpendicular to the rim plane of the acetabulum, a ring can be displayed around the bone that is divided in to radial sections and labelled with the clock hours. The hour corresponding to a particular tracked tool position such as the probe 124 or burr tip 74 can be highlighted when it is visible. Thus as the surgeon is burring from one hour to another the highlighted hour on the clock ring changes and he can easily detect when he has changed locations on the bone surface.

Calculating Impingement

Figure 8:
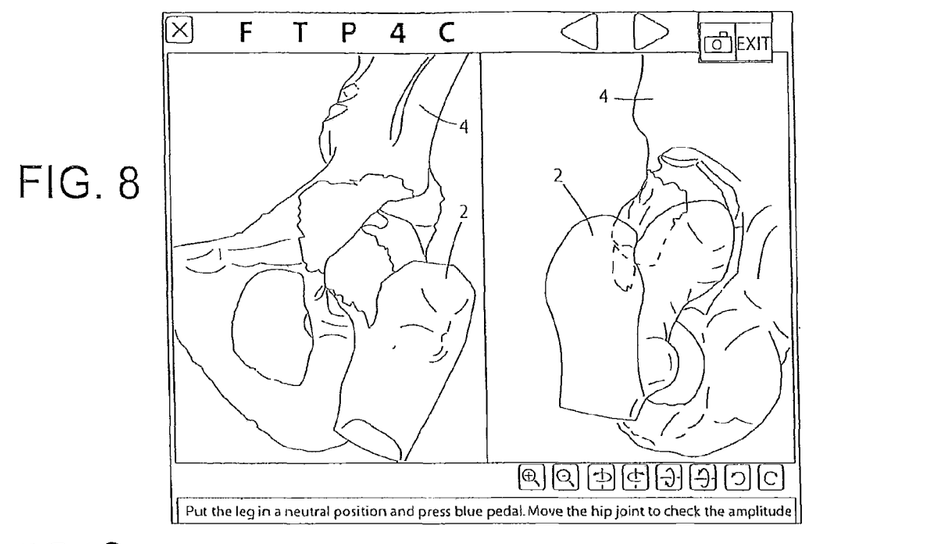
FIG. 8 is an image of the leg being placed in a neutral position for subsequent movement of the hip joint to check the amplitude.

The femur 2 can be manipulated with respect to the acetabulum, and the models on the screen 32 move in real time as the surgeon manipulates the joint (See. FIG. 8). In particular, the surgeon can move the joint until he sees the bones impinging upon themselves on the models. This impingement corresponds to an actual and real impingement of motion as felt by the surgeon when he manipulates the leg. In addition, the computer can detect the instant when the bone morphing models come into contact with each other, and this can be alerted to the surgeon by a change in color on the display 32, for example. Thus the surgeon can verify that impingement felt is a real bone impingement and not one due to other causes, such as, for example, due to a soft tissue contracture on the other side. The surgeon can also verify the exact area of impingement on the bones, and this can be automatically stored in the computer. Collision detection algorithms for geometric models are well known, and any such algorithm could be used. The following article gives an example of a fast algorithm for calculating range of motion and impingement in the hip joint, and is hereby incorporated by reference: Real-Time Estimation of Hip Range of Motion for Total Hip Replacement Surgery by Kawasaki et al, Published in Medical Image Computing and Computer-Assisted Intervention—MICCAI 2004: 7th International Conference Saint-Malo, France, Sep. 26-29, 2004 Proceedings, Part II, Editors: Christian Barillot, David R. Haynor, Pierre Hellier, pp. 629-636, LNCS, Springer 2004. United States Patent Application publication No. 2003/0176783 A1, for example, discloses a fast algorithm for detecting impingement between implants and/or bones using implicit object models from reconstruction of anatomical CT data, and is hereby incorporated by reference in its entirety. Such an algorithm could be used with intra-operatively obtained models, such as, the Bone Morphing models described above. One or several contact positions can be stored in the computer, but for clarity we will consider only one contact position and then repeat this process for any positions needed. The contact position can be related to a reference rotation, such as 0 degrees, for example.

Relationship between Joint Rotation and Milling Depth

There are a plurality of methods that the system can employ to aid the surgeon in removing the correct amount of bone in order to restore proper joint function and range of motion. In an embodiment, the computer aided osteoplasty system establishes a relationship between the increase in joint motion and the milling depth with respect to the bone surface. In particular, the computer can simulate a rotation of the femur 2 into the pelvis 4 (or vice versa), for a predetermined amount or rotation, in any particular direction. Such a rotation can be about the hip center, for example, which has already been determined as described above. The direction of the rotation can be defined by a plurality of methods, such as, for example, by the surgeon, using the anatomic coordinate system. For example, he could enter 10° of flexion or 10° abduction on the tactile screen. Alternatively, he could physically move the femur 2 in a particular direction, and the system can record a trajectory of motion and calculate the direction to simulate the rotation in. The system can also calculate the direction as a function of the impingement area, such as a normal vector the surface. The system can simulate motion on one bone respect to another bone using either methods and display this motion on the screen for the surgeon to evaluate. By simulating a rotation of the femur 2 into the acetabulum, the intersection of the two surfaces can be calculated for a discrete number of rotations, for example, for every one degree from zero to ten degrees. Alternatively, the surgeon can enter into the computer 30 a target amount of motion that he would like give to the patient, and the system will automatically calculate the intersection of these surfaces for the given target rotation.

Referring now to FIGS. 3A-D, FIG. 3A schematically depicts a femur 301 and acetabulum 302 with hip center 300. The hip center location is known in both the femoral and acetabular coordinate systems. For joints which are particularly lax, or for example, when the hip is distracted using a traction table, the hip center 300 is no longer coincident for the femur 301 and acetabulum 302. The center 300 could be transferred from one bone to another one for a stable position of the joint, for example, when it is compressed, by taking a measurement with the camera 49 of position measuring device 20. FIG. 3B schematically depicts the femur rotated relative to the acetabulum by a target number of degrees 'α'. The corresponding intersection of the two surfaces 305 is identified using their locations. This defines a relationship between the target improvement in range of motion and the volumetric amount and location of bone volume to be removed in order to achieve that target goal for either the femur 301 or the acetabulum 302. This intersecting surface or volume 305 can be displayed on the screen 32 as a different color or different intensity of color on the bone, in order to indicate which areas of bone the surgeon must remove in order to achieve the target increase in range of motion.

FIG. 3C schematically shows how a series of surfaces can be determined that correspond to a range of increased rotation values. Each surface in the series of surfaces 310 can correspond to an additional one or two degrees of hip motion, for example. These surfaces or impingement maps can be displayed as a color map on the display screen 32, with different colors representing different degrees of rotation. A color key can also indicate which colors correspond to which degrees of rotation or milling depths. In cases where the surgeon would only like to perform the osteoplasty on one side of the joint, for example, on the femur 301, the color map can be displayed only on the bone to which the osteoplasty will be preformed.

A color map can also be calculated and displayed for one bone without information on the shape of the second bone. This can be very useful, for example, when the osteoplasty is to be performed only on one side of the joint, and the practitioner chooses to only attach a reference frame to the bone in which the osteoplasty is to be performed. The practitioner could use the probe 120 or calibrated burring device 70 to define a potential impingement zone, such as a center point of the impingement area or a border around the impingement area, as shown in FIG. 4. Each point, triangle, or pixel in the bone model could be represented with a color that is dependent on the depth or distance to the surface of the bone. Again, the color spectrum could be a discrete one or a continuous one. Transparency could be used for the bone area or the color map area for clarification. The relationship between any point in the bone and the increased range of hip motion can also be calculated as a function of the distance from the point to the hip center 300, for example, and from the point to the bone surface, as illustrated FIG. 3D. A trigonometric function such as tan(beta)=d/(mag(PT-HC)), where PT is the point or pixel to be colored, HC is the hip center point 300, mag(PT-HC) is the distance between these two points, and d is the distance between PT and the bone surface. The distance d can be the closest distance to the bone surface, or the distance calculated in specific direction. The current resection depth or potential increase in joint Range of Motion (ROM) can be displayed on the screen in real time.

Figure 5:
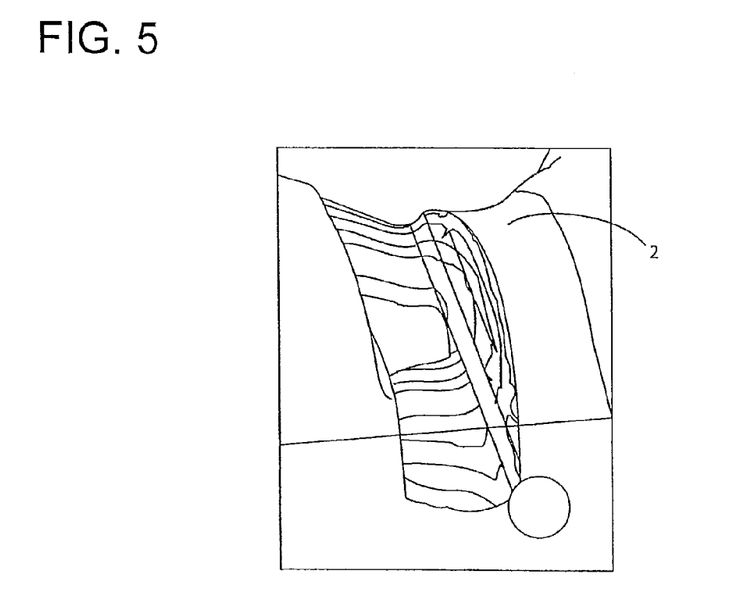
FIG. 5 is a perspective view of an image of a femoral bone surface, in real time, as it is being milled, with color map information displayed on the newly burred surface.

By tracking the burring device tip 74 (which has a known surface geometry and size and position with respect to its reference marker 72) with respect the femoral bone surface during the milling action, the system can register and track the volume of bone that has been removed. The system can thus display the tool and show the bone as it is being removed in real time, to reveal the color or impingement map information displayed on the newly burred bone surface (FIG. 5). The surgeon can then know to stop milling once he or she reaches a particular color of bone in the color map. This target color could be the same color as the whole bone itself, or any other color. This simulation of bone removal can carried out using voxel based methods as known in the literature, for example, or any other rendering algorithm available.

The bone surface can be recomputed or remorphed at any phase during the surgical procedure using the pointer 120 or the burring device 70. The surface and geometry of the milling device 70 is known, and can be used as a pointer to remorph the surface. An example technique for carrying out this using a spherical shape is described in United States patent application publication No. 2005/0101966 A1, which has already been referenced. This can be easily extended to other shapes, such as cylinders and elliptical shaped tools, simply by modifying the geometrical or parametric model accordingly (or example, by making the tool radius a function of the axial position). This surface or the superposition of all the recorded tool positions measured and stored during the milling phase can thus be used to remorph the bone surface shape, at any time during the procedure.

Note if the impingement map is dependent on the shape of the bone surface, the impingement map can therefore also be updated at any time during the procedure. For example, as described above and illustrated in FIG. 3C, the impingement or color map can be recomputed for the femur 301, as the acetabular surface 302 is being shaved and remorphed. This can be happening in real time in the background so as to be transparent to the surgeon. The impingement or color map can also be recomputed in real time or at any particular time during the procedure, for the case in which the color map is calculated as a function of the bone being burred, as described FIG. 3D or and/as above. Thus the impingement or color map can be a dynamic one.

In one preferred embodiment of the invention, the following process can also be applied. Once both potential infringing shapes on femur and pelvis have been acquired, the surgeon can select the amount of extra range of motion he would like to gain. The computer can then extrapolate the femur motion up to that desired position and computes the intersection on both surfaces. The intersection of surfaces on the femur creates a patch surface that is connected to the rest of the surface of the femur. This new surface results in an objective to reach for the surgeon. A color map indicates the distance between the current surface and the objective surface on each point of the surface. For instance, red indicates more than 5 mm, dark orange between 4 and 5 mm, light orange between 3 and 4 mm, yellow between 2 and 3 mm, green between 1 and 2 mm, grey between 0 and 1 mm and blue for negative values. When the surgeon uses the burring device 70, the color map changes in real time and colors progressively vanish until the surgeon reaches a grey or blue color map everywhere, which indicates that the objective surface has been reached. Such a representation could be used in cases where the color map of the femur is dependent only on the shape of the femur (i.e. color at any point is proportional to the distance to the original femoral neck surface).

The range of motion can also be a number in degrees of flexion that is computed, displayed and updated on the screen for the surgeon at any time and in real time. Indeed, for a given shape of the bone, it is possible to extrapolate the degree of motion of the femur and calculate at what angle the impingement is reached. This new value represents the degree of motion that the surgeon wins each time the surgeon is milling the bone. Any method can be used to calculate the range of motion, such as those described and referenced above.

All previous modes can be combined together.

Figure 7:
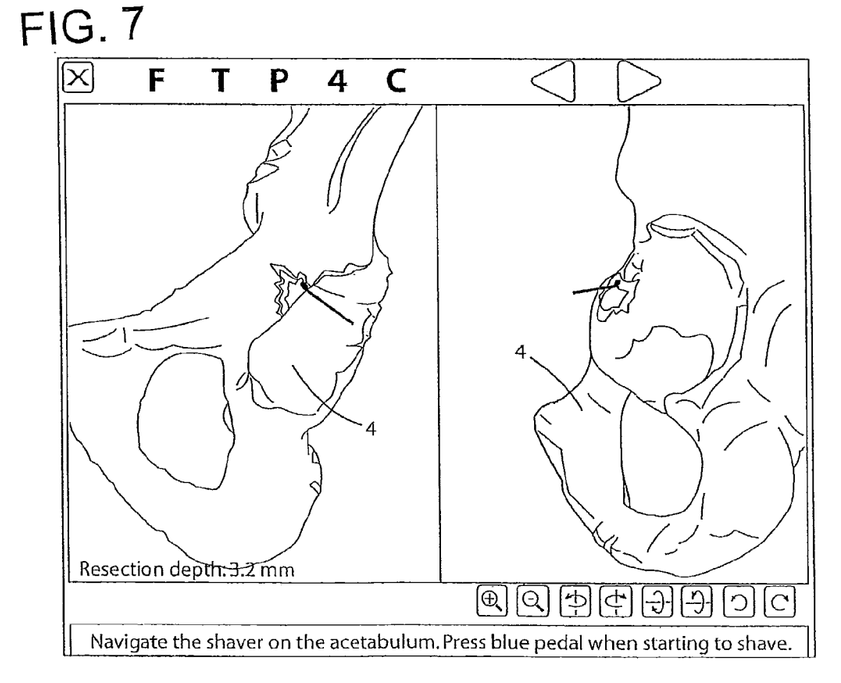
FIG. 7 is a perspective view of an image of the acetabulum surface with a shaving tool being navigated therealong for shaving a select, target portion of the acetabulum surface.

The present system easily permits the surgeon to use the pointer 120 and delineate the femur surface (femur bump) that is to be shaved in order to achieve the desired fit between the femur and acetabulum surface. Then as shown in FIG. 4 in the case of the femur bone and in FIG. 7 in the case of the pelvis bone, the shaving tool (e.g. burring device) can be navigated along the respective surfaces and the movements of the shaver are reflected in real time on the computer screen 32.

The navigation system 10 is an integrated system and can have the burring device 70 connected to it. Therefore, the system can control the function of the milling tool as a function the position of the tool with respect to the bone as measured by the camera 49. For example, the burr may be 'pulsed' as the surgeon approaches the boundary of the impingement map, according to the target increase in range of joint motion or milling depth. This can be accomplished by altering the electrical supply signal to the burring device 70. Alternatively, the burr can be automatically stopped when it passes the boundary. In particular, the burr can be stopped or pulsed when its surface reaches the target impingement surface as identified by the system. The actual burring can also be guided by a robot to obtain a precisely cut surface with respect to the impingement color map.

Flexible Protocol

One feature of the invention is that it is a flexible system and allows the surgeon to select the protocol that he wishes at the beginning of the procedure. Several options are possible, including the order of the acquisitions and steps, the instruments and optional imaging devices to be used, and the bones to be operated on. The following is one example of a protocol that the surgeon can define:

Pins and Rigid Bodies installed after draping
Pointer and Milling tool calibration steps completed first (can be performed by OR technicians)
Tracked C-arm images can be used to aid point acquisitions, morphing and shaving at any step
Symphisis+Homolateral spine acquisitions
Tibial Crest+Patella acquisitions
Dynamic Hip center and Pre-Op Range of Motion (ROM) measurement
apply traction, make portals, clean bone surfaces (portal incisions can be assisted using navigation C-arm images, using probe to mark desired location on skin)
most lateral point on greater trochanter (optionally under navigated fluoroscopy)
Femoral head surface acquisitions
Points on the acetabular rim Acetabular surface digitization: BoneMorphing (BM) Acetabulum+Model Check
Adjust Acetabular clock position with one point if necessary
Acetabular Navigated Shaving
release traction
Femoral neck surface digit: BM Femur+Model Check
Adjust Femur clock position with one point
Femur Navigated Shaving
Post-Op ROM measurements
Visualization of any impingement zones+Display of increased ROM
Repeat any steps if necessary
Save report on CD-ROM, USB key or Network The flexible protocol allows the surgeon to select the order and actions and tools of his preference, and many variations of the above protocol can be chosen. He can also save and store his preferred protocol under a user name of his choice. Modification of the options can also be carried out during the procedure, in case for any unforeseen reason the surgeon would like to change the order or jump to a different step. This is accomplished touching a button on the touchscreen which brings up a list of options and workflow order, which can be modified using the interface, allowing the surgeon to return to the new modified protocol.

The invention should not be limited to the description given above. For example, this system could be applied to the knee elbow or shoulder, joint or any joint for that matter. In addition, the invention could be combined with other such known features of computer assisted surgical systems, such as the calculation of joint laxity parameters, either linear or rotational, in various directions such as those described in U.S. patent application Ser. No. 11/299,287, entitled "Computer Assisted Orthopaedic Surgery System for Ligament Graft Reconstruction" by P. Colombet et al., which is hereby incorporated by reference in its entirety.

While the invention has been described in connection with certain embodiments thereof, the invention is capable of being practiced in other forms and using other materials and structures. Accordingly, the invention is defined by the recitations in the claims appended hereto and equivalents thereof.

All above cited references are hereby incorporated by reference.

What is claimed is:

1. A method for performing computer-assisted orthopaedic surgery comprising the steps of:
   using a device to acquire first coordinate points on a surface of a first bone;
   using the device to acquire second coordinate points on a surface of a second bone that forms a joint with the first bone;
   producing and displaying a three-dimensional geometrical surface model of the first bone based at least initially on the acquired first coordinate points;
   producing and displaying a three-dimensional geometrical surface model of the second bone based at least initially on the acquired second coordinate points;
   moving the first and second bones relative to one another and detecting maximum amplitudes of rotation between the first and second bones;
   identifying a zone of impingement between the first and second bones on at least one of the bones;
   generating and displaying as a color map at least one surface of at least one bone model, the at least one surface being within the zone of impingement, the color map including different colors representing different depths of bone to be removed in order to achieve an increased range of motion between the two bones, the colors of the color map indicating a distance between a current bone surface and an objective bone surface for each point of the at least one surface, the objective bone surface being the bone surface that permits a target increased range of motion between the two bones to be achieved;
   using a tracked tool to remove bone in the zone of impingement based on real time information provided on the color map; and
   moving again the first and second bones relative to one another and detecting an increased amount of rotation between the first and second bones.

2. The method of claim 1, further including the step of: representing the different colors by a continuous or discrete spectrum of varying brightness of a single color.

3. The method of claim 1, wherein the step of acquiring points on each of the surfaces of the first and second bones comprises the step of: projecting a current pointer position overtop of registered fluoroscopic images of the bones.

4. The method of claim 3, further including the step of: extracting bone contours from the registered fluoroscopic images to assist in generating the three-dimensional geometrical surface models.

5. The method of claim 1, further including the step of: superimposing the generated three dimensional geometrical surface models over registered fluoroscopic images of the bones to allow a surgeon to verify model accuracy.

6. The method of claim 1, further including the steps of: continuously, in real time, updating the three-dimensional geometrical surface models of the bones as bone is removed; and superimposing the updated three dimensional geometrical surface models over registered fluoroscopic images of the bones to allow a surgeon to compare the updated surface of the three dimensional geometrical models with original surface models in the fluoroscopic images.

7. A method for displaying bone related information to guide a surgeon in removal of bone as part of a system used in computer-assisted orthopaedic surgery comprising the steps of:
   producing and displaying three-dimensional geometrical models of first and second bones, the first and second bones forming a joint;
   identifying a zone of impingement between the first bone and the second bone on at least one of the bones;
   establishing a relationship between an increase in motion of the joint and a resection depth with respect to a surface of at least one of the first and second bones that is to be removed within the zone of impingement; and
   generating and displaying a color map of at least one surface of at least one bone, the at least one surface being within the zone of impingement, the color map including different colors representing different depths of bone to be removed in order to achieve an increased range of motion between the first and second bones.

8. The method of claim 7, further including the steps of: continuously, in real time, updating the three-dimensional geometrical surface models of the bones as bone is removed; and continuously, in real time, updating the color map to show updated depths of at least one of the first and second bones as bone is removed.

9. The method of claim 7, further including the steps of: moving the first and second bones relative to one another and detecting maximum amplitudes of rotation between the first and second bones prior to and to permit identification of the zone of impingement; and moving the first and second bones subsequent to one another after removal of bone in the zone of impingement and detecting an increased amount of rotation between the first and second bones.

10. The method of claim 7, wherein the first bone is a femur bone and the second bone is a pelvis bone and the joint is defined by the femur and the acetabulum surface of the pelvis bone, the range of motion being a rotation of the femur into the acetabulum, with the zone of impingement being defined by the femur and the acetabulum, and further including the step of indicating on the color map different increased degrees of rotation with different colors that represent different depths between a current bone surface and an objective bone surface which results in a desired increased degree of rotation between the first and second bones being realized.

11. A method for performing computer-assisted orthopaedic surgery comprising the steps of:
using a device to acquire first coordinate points on a surface of a first bone;
using the device to acquire second coordinate points on a surface of a second bone that forms a joint with the first bone;
producing and displaying a three-dimensional geometrical surface model of the first bone based on the acquired first coordinate points;
producing and displaying a three-dimensional geometrical surface model of the second bone based on the acquired second coordinate points;
moving the first and second bones relative to one another and detecting when the geometrical models of the first and second bones come into contact with one another in a defined zone of impingement;
generating and displaying as a color map at least one surface of at least one bone model, the at least one surface being within the zone of impingement, the color map including different colors representing different degrees of increased range of motion between the two bones, as well as different depths of bone to be removed in order to achieve the different increased range of motions between the two bones;
selecting one increased range of motion that is desired between the two bones; and
using a tracked tool to remove bone in the zone of impingement based on real time information provided on the color map until the selected increase in range of motion is achieved as indicated when the color map reveals a target color for at least the zone of impingement.

12. The method of claim 11, further including the step of: representing different degrees of rotation between the first and second bones with different colors.

13. The method of claim 11, further including the step of: representing each point of each model in a particular zone with a color that is dependent on a depth or distance between a current surface of the bone and an objective surface of the bone that results in the selected increase in range of motion.

14. The method of claim 13, further including the step of: using as part of the color map colors that are part of a discrete color spectrum.

15. The method of claim 13, further including the step of: using as part of the color map colors that are part of a continuous color spectrum.

16. The method of claim 11, further including the step of: representing greater depths of bone that need to be removed in order to achieve the selected increased range of motion with darker colors of the color map.

17. The method of claim 11, further including the step of: indicating in the color map different increased degrees of rotation with different colors that represent different depths between the current bone surface on which the acquired points were taken and the objective bone surface which would result in the selected increased degree of rotation between the two bones being realized, wherein the range of motion is a rotation of a femur into an acetabulum, with the zone of impingement being defined by the femur and the acetabulum.

18. The method of claim 17, further including the step of: changing the colors of color map in real time as a device is used to remove the bone such that the colors progressively vanish as more bone is removed until the entire color map in the zone of impingement has a first target color which indicates that the objective bone surface has been reached.

19. The method of claim 11, further including the step of: using a plurality of colors in the zone of impingement to represent different depths of bone that are needed to be removed in order to achieve the selected additional range of motion.

20. The method of claim 11, further including the step of: creating and displaying the color map for the first bone without information on a shape of the second bone.

21. The method of claim 11, further including the step of: creating and displaying in real time, an updated color map showing a current depth of bone as bone is removed in order to achieve the different increased range of motions between the two bones and to guide an operator of the tracked tool as to how much additional bone is to be removed, wherein the color map is a dynamic color map.

22. The method of claim 11, further including the step of: displaying at least the first geometrical bone model with a clock reference superimposed thereon and including twelve latitudinal lines projected on the three dimensional bone model, the latitudinal lines being divided radially from a center point with equal spacing to represent twelve hours of a clock, each latitudinal line being uniquely identified to assist a surgeon in identifying and conveying a particular position on the bone surface.

23. The method of claim 22, further including the step of: highlighting a closest latitudinal line relative to the tracked tool that is positioned on the bone surface to assist the surgeon in determining when the surgeon has changed locations on the bone surface.

* * * * *